US00PP23671P2

(12) United States Plant Patent
Lannes

(10) Patent No.: US PP23,671 P2
(45) Date of Patent: Jun. 18, 2013

(54) ***MANDEVILLA* PLANT NAMED 'LANMICHIGAN'**

(50) Latin Name: ***Mandevilla boliviensis*×*Mandevilla Sanderi***
Varietal Denomination: Lanmichigan

(75) Inventor: Robert Lannes, Malause (FR)

(73) Assignee: D.H.M. Innovation S.A.S., Malause (FR)

( * ) Notice: Subject to any disclaimer, the term of this patent is extended or adjusted under 35 U.S.C. 154(b) by 0 days.

(21) Appl. No.: 13/374,923

(22) Filed: Jan. 23, 2012

(51) Int. Cl.
*A01H 5/00* (2006.01)

(52) U.S. Cl.
USPC ..... Plt./232

(58) Field of Classification Search
USPC ..... Plt./232
See application file for complete search history.

(56) References Cited

PUBLICATIONS

PLUTO Plant Variety Database 2012-05 search for Lanmichigan.*

* cited by examiner

*Primary Examiner* — Annette Para
(74) *Attorney, Agent, or Firm* — C. A. Whealy

(57) ABSTRACT

A new and distinct cultivar of *Mandevilla* plant named 'Lanmichigan', characterized by its compact and bushy plant habit; moderately vigorous to vigorous growth habit; glossy dark green-colored leaves; early and freely flowering habit; and white-colored flowers.

2 Drawing Sheets

Botanical designation: *Mandevilla boliviensis*×*Mandevilla Sanderi*.

Cultivar denomination: 'LANMICHIGAN'.

BACKGROUND OF THE INVENTION

The present invention relates to a new and distinct cultivar of *Mandevilla* plant, botanically known as *Mandevilla boliviensis*×*Mandevilla Sanderi* and hereinafter referred to by the name 'Lanmichigan'.

The new *Mandevilla* plant is a product of a planned breeding program conducted by the Inventor in Malause, France. The objective of the breeding program is to create new compact *Mandevilla* plants with numerous white-colored flowers.

The new *Mandevilla* plant originated from a cross-pollination conducted by the Inventor in Malause, France of an unnamed selection of *Mandevilla boliviensis*, not patented, as the female, or seed parent with *Mandevilla Sanderi* 'Blanc', not patented, as the male, or pollen, parent. The new *Mandevilla* plant was discovered and selected by the Inventor as a single flowering plant from within the progeny of the stated cross-pollination in a controlled greenhouse environment in Malause, France.

Asexual reproduction of the new *Mandevilla* plant by cuttings in a controlled greenhouse environment in Malause, France, since May, 2010 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Lanmichigan'. These characteristics in combination distinguish 'Lanmichigan' as a new and distinct *Mandevilla* plant:

1. Compact and bushy plant habit.
2. Moderately vigorous to vigorous growth habit.
3. Glossy dark green-colored leaves.
4. Early and freely flowering habit.
5. White-colored flowers.

Plants of the new *Mandevilla* can be compared to plants of the female parent selection. Plants of the new *Mandevilla* differ primarily from plants of the female parent selection in the following characteristics:

1. Plants of the new *Mandevilla* are more compact than plants of the female parent selection.
2. Plants of the new *Mandevilla* have shorter internodes than plants of the female parent selection.
3. Plants of the new *Mandevilla* have smaller leaves than plants of the female parent selection.

Plants of the new *Mandevilla* can be compared to plants of the male parent, 'Blanc'. Plants of the new *Mandevilla* differ primarily from plants of 'Blanc' in the following characteristics:

1. Plants of the new *Mandevilla* are more vigorous than plants of 'Blanc'.
2. Plants of the new *Mandevilla* are more freely branching than plants of 'Blanc'.
3. Plants of the new *Mandevilla* have thinner and glossier leaves than plants of 'Blanc'.
4. Flowers of plants of the new *Mandevilla* are star-shaped whereas flowers of plants of 'Blanc' are more rounded.

Plants of the new *Mandevilla* can be compared to plants of selections of *Mandevilla Sanderi* with white-colored flowers known to the Inventor, not patented. In side-by-side comparisons conducted in Malause, France, plants of the new

*Mandevilla* differed from plants of selections of *Mandevilla Sanderi* known to the Inventor in the following characteristics:

1. Plants of the new *Mandevilla* were more freely branching than plants of selections of *Mandevilla Sanderi* known to the Inventor.
2. Plants of the new *Mandevilla* had smaller leaves than plants of selections of *Mandevilla Sanderi* known to the Inventor.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lanmichigan' grown in a container.

The photograph on the second sheet is a close-up view of a typical flowering plant of 'Lanmichigan'.

DETAILED BOTANICAL DESCRIPTION

The aforementioned photographs and following observations, measurements and values describe plants grown during the autumn in two-liter containers in polyethylene-covered greenhouse in Malause, France and under cultural practices typical of *Mandevilla* commercial production. During the production of the plants, day temperatures ranged from 8° C. to 26° C. and night temperatures ranged from 3° C. to 15° C. Plants were six months old when the photographs and description were taken. In the following description, color references are made to The Royal Horticultural Society Colour Chart, 2007 Edition, except where general terms of ordinary dictionary significance are used.

Botanical classification: *Mandevilla boliviensis*×*Mandevilla Sanderi* 'Lanmichigan'.

Parentage:

*Female, or seed, parent*.—Unnamed selection of *Mandevilla boliviensis*, not patented.

*Male, or pollen, parent*.—*Mandevilla Sanderi* 'Blanc', not patented.

Propagation:

*Type*.—By vegetative cuttings.

*Time to initiate roots, summer*.—About two weeks at 23° C. to 25° C.

*Time to initiate roots, winter*.—About three weeks at 23° C. to 25° C.

*Time to produce a rooted young plant, summer*.—About five to six weeks at 23° C. to 25° C.

*Time to produce a rooted young plant, winter*.—About six to eight weeks at 23° C. to 25° C.

*Root description*.—Fibrous, fine; light yellowish white in color.

*Rooting habit*.—Freely branching; medium density.

Plant description:

*Plant and growth habit*.—Compact and bushy plant habit; upright to outwardly spreading; moderately vigorous to vigorous growth habit.

*Plant height*.—About 32 cm.

*Plant diameter* (*spread*).—About 53.5 cm.

*Lateral branch description*.—Branching habit: Moderately freely branching habit with about six lateral branches developing per plant; pinching enhances lateral branch development. Length: About 25.4 cm. Diameter: About 2 mm. Internode length: About 3.1 cm. Strength: Strong. Texture: Smooth, glabrous. Color: Close to 144A to 144B.

Foliage description:

*Arrangement*.—Opposite, simple.

*Length*.—About 5.1 cm.

*Width*.—About 3.8 cm.

*Shape*.—Obovate to broadly ovate.

*Apex*.—Abruptly acute.

*Base*.—Truncate.

*Margin*.—Entire.

*Texture, upper and lower surfaces*.—Smooth, glabrous; glossy.

*Venation pattern*.—Pinnate, reticulate.

*Color*.—Developing leaves, upper surface: More intense than 143A. Developing leaves, lower surface: Close to 146B. Full expanded leaves, upper surface: Close to N137B; venation, close to 145A. Fully expanded leaves, lower surface: Between 146B and 147B; venation, close to 145A.

*Petiole length*.—About 9 mm.

*Petiole diameter*.—About 1.5 mm.

*Petiole texture, upper and lower surfaces*.—Smooth, glabrous.

*Petiole color, upper surface*.—Close to 144B tinged with close to 152A.

*Petiole color, lower surface*.—Close to 144B.

Flower description:

*Flower type and flowering habit*.—Single salverform flowers arranged in axillary racemes; flowers star-shaped and face upright and outwardly; freely flowering habit with about three flowers developing per inflorescence and about 18 flowers developing per plant.

*Natural flowering season*.—Early flowering habit with plants begin to flower about six weeks after planting; plants flower continuously from summer into the autumn in France.

*Flower longevity on the plant*.—About seven days; flowers not persistent.

*Fragrance*.—Moderately faint, pleasant.

*Flowers*.—Appearance: Flared trumpet, corolla fused and five-parted. Diameter: About 8.2 cm. Depth (length): About 6.8 cm. Tube length: About 5.2 cm.

*Flower buds*.—Length: About 6.8 cm. Diameter: About 1.2 cm. Shape: Narrowly obovate. Color: Close to 145C to 145D; towards the base, close to 145A.

*Corolla*.—Quantity and arrangement: Five petals arranged in a single whorl and fused at the base. Petal length: About 9.4 cm. Petal width: About 3 cm. Petal shape and appearance: Roughly spatulate; lower 55% of the petal is fused. Petal apex: Bluntly acute. Petal margin: Entire. Petal texture, upper and lower surfaces: Smooth, glabrous; slightly velvety. Throat texture: Smooth, glabrous. Tube texture: Smooth, glabrous. Color: Petal, when opening, upper surface: Close to 69C, towards the base, close to 155C; throat, close to 14B, towards the base of the throat, close to 31A. Petal, when opening, lower surface: Close to 69C, towards the base, close to 155C; tube, close to 150C to 150D, towards the base of the tube, close to 14D. Petal, fully opened, upper surface: Close to NN155D flushed with close to N155B; throat, close to 17C striped with close to 25B, towards the base of the throat, close to 31A. Petal, fully opened, lower surface: Close to NN 155D slightly flushed with close to N155B; tube, close to 19D, towards the base of the tube, close to 14D.

*Corona*.—Quantity and arrangement: Five sepals arranged in a single whorl. Sepal length: About 8 mm. Sepal width: About 2 mm. Sepal shape: Lanceolate. Sepal apex: Narrowly acuminate. Sepal base: Roughly truncate. Sepal margin: Entire. Sepal texture, upper and lower surfaces: Smooth, glabrous. Sepal color: Immature and mature, upper surface: Close to 144D. Immature and mature, lower surface: Close to 144D.

*Peduncles*.—Length: About 4.8 cm. Diameter: About 1.5 mm. Texture: Smooth, glabrous. Strength: Flexible, but strong. Color: Close to 143B.

*Pedicels*.—Length: About 1.5 cm. Diameter: About 1.5 mm. Texture: Smooth, glabrous. Strength: Flexible, but strong. Color: Close to 144B.

*Reproductive organs*.—Stamens: Quantity and arrangement: Typically five; basifixed; anthers connivent. Filament length: About 1 mm. Anther shape: Ellipsoidal. Anther length: About 1 mm. Anther color: Close to 160B. Pollen amount: None observed. Pistils: Quantity: Typically one. Pistil length: About 2.3 cm. Style length: About 2 cm. Style color: Close to 145D. Stigma shape: Conical. Stigma color: Close to 154C. Ovary color: Close to 144C.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be hardy to USDA Hardiness Zone 9.

It is claimed:

1. A new and distinct *Mandevilla* plant named 'Lanmichigan' as illustrated and described.

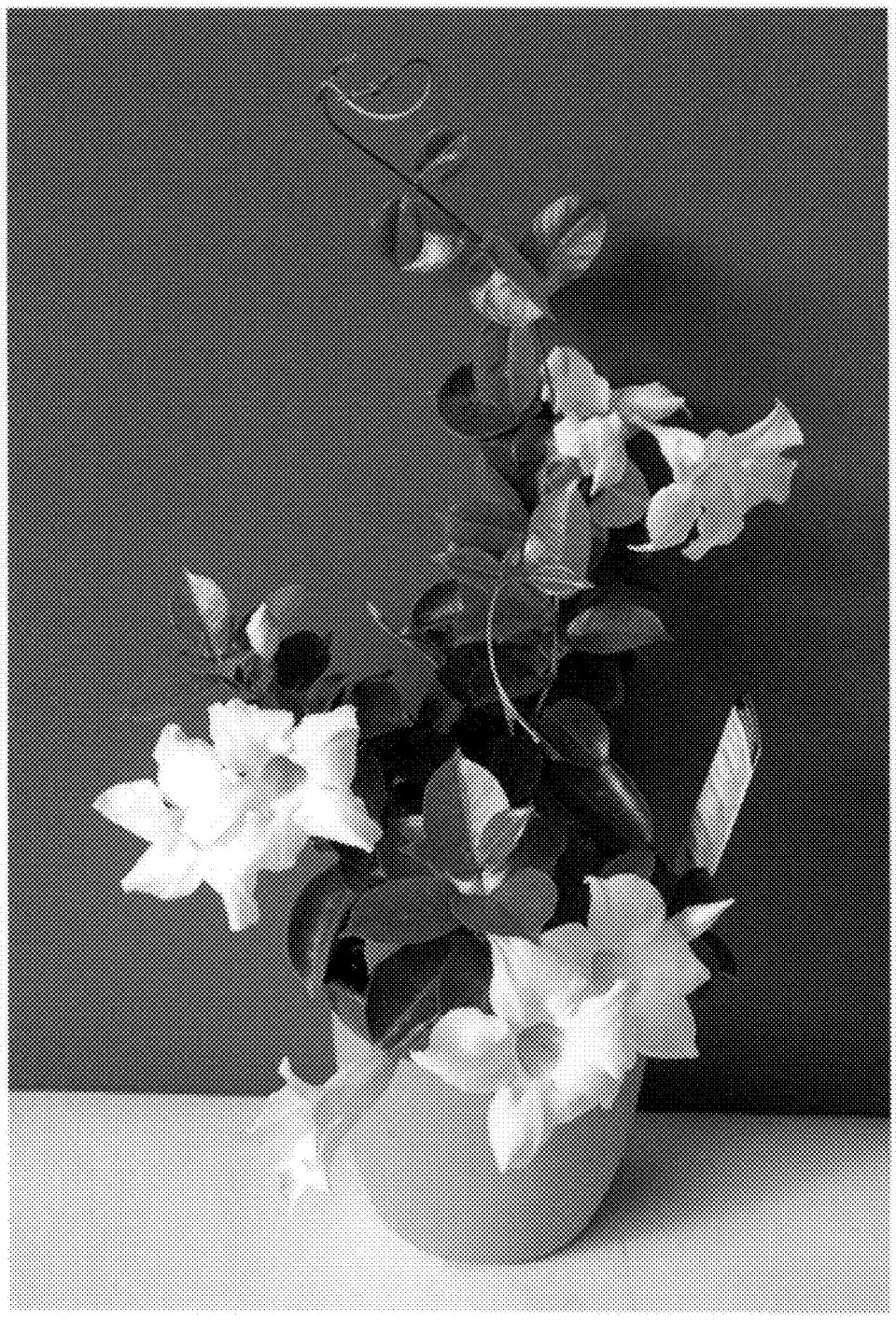

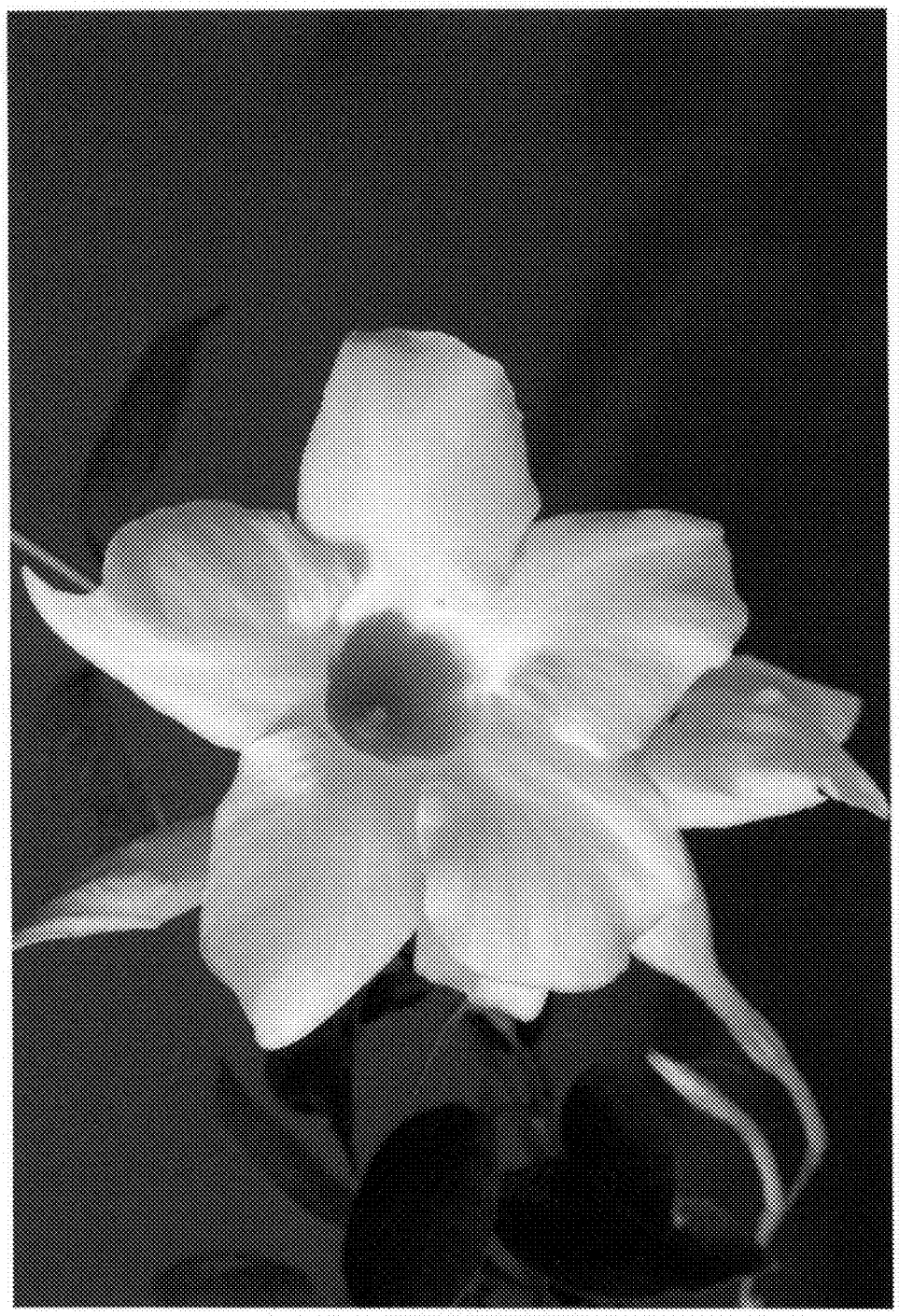

* * * * *